(12) United States Patent
Blair et al.

(10) Patent No.: US 8,871,739 B2
(45) Date of Patent: Oct. 28, 2014

(54) SOLID ACID CATALYZED HYDROLYSIS OF CELLULOSIC MATERIALS

(75) Inventors: Richard G. Blair, Oviedo, FL (US); Sandra M. Hick, Oviedo, FL (US); Joshua H. Truitt, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 138 days.

(21) Appl. No.: 12/621,741

(22) Filed: Nov. 19, 2009

(65) Prior Publication Data

US 2010/0113764 A1 May 6, 2010

Related U.S. Application Data

(63) Continuation-in-part of application No. PCT/US2008/082386, filed on Nov. 5, 2008.

(51) Int. Cl.
| | |
|---|---|
| *C12P 19/12* | (2006.01) |
| *C07H 3/04* | (2006.01) |
| *C07H 3/02* | (2006.01) |
| *A61K 31/7016* | (2006.01) |
| *A61K 31/70* | (2006.01) |

(52) U.S. Cl.
CPC . *C12P 19/12* (2013.01); *C07H 3/02* (2013.01); *C07H 3/04* (2013.01)
USPC .................................. 514/53; 514/57; 524/58

(58) Field of Classification Search
CPC ........................... A61K 31/7016; A61K 31/70
USPC ......................................... 514/53, 57; 524/58
See application file for complete search history.

(56) References Cited

U.S. PATENT DOCUMENTS

| | | | |
|---|---|---|---|
| 4,078,991 | A | 3/1978 | Goldstein |
| 4,356,060 | A | 10/1982 | Neckermann et al. |
| 4,415,124 | A | 11/1983 | Carduck et al. |
| 4,461,648 | A | 7/1984 | Foody |
| 4,470,851 | A | 9/1984 | Paszner et al. |
| 4,496,106 | A | 1/1985 | Gross |
| 4,511,433 | A | 4/1985 | Toumier et al. |
| 4,650,689 | A | 3/1987 | Hedrick |
| 6,022,419 | A | 2/2000 | Torget et al. |
| 6,419,788 | B1 | 7/2002 | Wingerson |
| 6,620,292 | B2 | 9/2003 | Wingerson |
| 6,660,506 | B2 | 12/2003 | Nguyen et al. |
| 6,908,995 | B2 | 6/2005 | Blount |
| 2003/0233011 | A1 | 12/2003 | Fagan et al. |
| 2007/0125369 | A1 | 6/2007 | Olson et al. |

FOREIGN PATENT DOCUMENTS

| | | |
|---|---|---|
| JP | 02016101 A * | 1/1990 |
| WO | WO 2007138256 A2 * | 12/2007 |

OTHER PUBLICATIONS

Fitzgerald, Richard, Solid Acids Show Potential for Fuel Cell Electrolytes, Physics Today, Jul. 2001.
Energy Information Administration, Biofuels in the U.S. Transportation Sector, Feb. 2007.
Chem, Turk J., Investivation of the Surface Acidity of a Bentnite Modified by Acid Activation and Thermal Treatment, Mar. 19, 2003.
Roman-Leshkov et al., Production of dimethylfuran for liquid fuels from giomass-dirived carbohydrates, Nature, vol. 447/21, Jun. 2007.
Zhao et al., Metal Chlorides in Ionic Liquid Solvents Convert Sugars to 5-Hydroxmethylfurfural, Science, vol. 316, Jun. 15, 2007.
Jakobsson, Eva-Lena, Optimization of the pretreatment of wheat straw for the production of bioethanol, Department of Chemical Engineering, Lund University (2002).
WO/2009/061750, PCT/US2008/082386, International Preliminary Report on Patentability, Feb. 13, 2009.
WO/2009/061750, PCT/US2008/082386, International Search Report, Feb. 23, 2009.
Definition of Reactant, IUPAC Gold Book, http://goldbook.iupac.org, accessed online on Dec. 15, 2010.
Lenarda et al., *Solid Acid Catalysts from Clays: Preparation of Mesoporous Catalysts by Chemical Activation of Metakaolin Under Acid Conditions*, Journal of Colloid and Interface Science, 2007, 311, pp. 537-534, published online Apr. 23, 2007.
Hahn-Hagerdal et al., *Solid Superacids for Hydrolyzing Oligo-and Polysaccharides$^a$*, Annals of the New York Academy of Sciences, 434(1), pp. 161-163, 1984.

* cited by examiner

*Primary Examiner* — Patrick Lewis
*Assistant Examiner* — Everett White
(74) *Attorney, Agent, or Firm* — Dunlap Codding P.C.

(57) ABSTRACT

Provided are methods for the solubilization of cellulose into soluble sugars without the need for high temperatures, high pressures, strong acid solutions, and/or added water. The produced sugars can be fermented into ethanol. In one embodiment, the method comprises contacting a cellulose-containing material with a solid acid material and agitating the cellulose-containing material and the solid acid material for a time sufficient to produce an aqueous solution comprising a quantity of soluble sugars.

13 Claims, 8 Drawing Sheets

US 8,871,739 B2

SOLID ACID CATALYZED HYDROLYSIS OF CELLULOSIC MATERIALS

RELATED APPLICATIONS

This application is a continuation-in-part of PCT/US08/082,386 filed Nov. 5, 2008, which claims priority to U.S. Ser. No. 11/935,712 filed Nov. 6, 2007, which are incorporated herein by reference in their entirety.

FIELD OF THE INVENTION

The present invention relates to processes for the hydrolysis of cellulose-containing material, and more particularly to processes for the hydrolysis of cellulose-containing material into soluble sugars using a solid acid material.

BACKGROUND OF THE INVENTION

Ethanol is the most widely used liquid biofuel in the world. In the U.S., ethanol is typically used as a gasoline additive and is blended into gasoline at up to 10 percent by volume to produce a fuel called E10 or "gasohol." In 2005, total U.S. ethanol production alone was 3.9 billion gallons, or 2.9 percent of the total gasoline pool. In 2006, that number increased to 4.86 billion gallons, and is well on pace to further rise in 2007. Therefore, the efficient and inexpensive production of materials to produce ethanol is of great interest.

One source of feedstock material to produce ethanol is soluble sugars produced by hydrolyzing cellulose. Such hydrolysis processes currently draw significant interest because large amounts of cellulosic feedstocks, such as biomass materials, can be easily and cheaply obtained, and environmentally, the burning or landfilling of waste cellulosic materials can be reduced. Exemplary types of biomass materials include switchgrass, wood, paper, agricultural residues, industrial solid wastes, and herbaceous crops. The hydrolysis processes are characterized by the breaking of the bonds between the glucose monomer units of cellulose to provide soluble sugar moieties, which are fermentable into ethanol.

Two hydrolysis methods are commonly used: acid hydrolysis and enzymatic hydrolysis. However, neither process is optimal. Acid hydrolysis can be performed with dilute or concentrated acid. Unfortunately, dilute acids require high temperature and pressures while concentrated acids must be removed from the product before fermentation can occur. On the other hand, enzymatic processes require a stable supply of enzymes and pretreatment to more easily hydrolyze the cellulose, especially with lignocellulosic material. Also, as set forth in U.S. Pat. Nos. 6,419,788 and 4,461,648, for example, because of the complex chemical structure of lignocellulosic material, which includes lignin and hemicellulose that coat the cellulose, microorganisms and enzymes cannot effectively attack the cellulose without prior treatment because the cellulose is highly inaccessible to enzymes or bacteria. Accordingly, there is a need for a more efficient and inexpensive method of producing fermentable sugars for the mass production of ethanol.

SUMMARY OF THE INVENTION

The inventors have unexpectedly found that when a solid acid material is combined with a cellulose-containing material and agitated, a high yield of soluble sugars can be produced. In the process, the agitation of the material, typically in a mill, provides the kinetic energy necessary to drive the hydrolysis reaction while the solid acid material has a surface acidity that aids in hydrolyzing the glycosidic bonds of the cellulose material. In addition, when the solid acid material has a sufficient existing water content, the water of the solid acid material can provide the water necessary for the hydrolysis reaction without the need for added water. For example, in one embodiment of the present invention, the solid acid material is a material, such as kaolin or bentonite, which has a surface acidity as well as a water content. The resulting products of the hydrolysis reaction, which include a quantity of soluble and fermentable sugars, are useful in the production of ethanol and for other purposes.

Moreover, the inventors have found that when the cellulose-containing material is a lignocellulosic material, the solid acid material may also hydrolyze the hemicellulose and lignin of the lignocellulosic material. Hemicelluloses are non-cellulosic polysaccharides that are built up mainly of sugars other than glucose, i.e. D-xylose with other pentoses and some hexoses with β-linkages. They are generally poorly ordered and non-crystalline and have a much lower chain length than cellulose. Lignin is an aromatic polymer, phenolic in nature, and built up from phenylpropane units, but with no systematic structure. Thus, when the cellulose-containing material is a lignocellulosic material, the hemicellulose and lignin of the material can also be decomposed into useful products, namely further soluble sugars and aromatic hydrocarbons, such as vanillin, respectively. In this way, the present invention can eliminate waste from the hydrolysis of lignocellulosic material, as well as eliminate the need to pre-treat the cellulose material before hydrolyzing the lignocellulosic material, as in known processes.

In view of the above, in accordance with one aspect of the present invention, there is provided a method for the production of soluble sugars from a cellulose-containing material, comprising: (a) contacting the cellulose-containing material with a solid acid material; and (b) agitating the cellulose-containing material and the solid acid material for a time sufficient to produce a product comprising soluble sugars. Optionally, an initial aqueous solution may be recovered after the step of agitating that comprises soluble sugars. The cellulose-containing material may be a pure cellulose material or any other type of cellulose-containing material, such as a biomass or lignocellulosic material. The solid acid material may be any type of solid or semi-solid material having a surface acidity, defined as $H_0$, with a value of less than about −3.0, and more preferably less than about −5.6.

Optionally, the method further comprises: (c) after the step of agitating, recovering a second aqueous solution comprising soluble sugars by rinsing the solid acid material and the cellulose-containing material with an aqueous solution. In addition, since the solid acid material is not a reactant in the hydrolysis process, after the step of recovering, the process optionally further comprises: (d) reusing a quantity of solid acid material and repeating steps (a) and (b), and optionally (c) above, with further cellulose-containing material. The process may be performed within a mill or any other suitable vessel that provides agitation of the material therein.

In accordance with another aspect of the present invention, there is provided a method for the production of soluble and fermentable sugars from a cellulose-containing material, comprising:

(a) contacting the cellulose-containing material with a solid acid material; and (b) agitating the cellulose-containing material and the solid acid material for a time sufficient to produce a product comprising soluble sugars, wherein agitating occurs at a temperature of between about −5 to about 105 degrees Celsius, and wherein said cellulose-containing material and solid acid material have a combined free water content of about 45% or less. Thereafter, the method optionally includes steps (c) and (d) as described above.

Thus, the present invention also contemplates that certain types of solid acid materials may inherently have a water content that enables the hydrolysis of the cellulose-containing material to occur without the need for added water. This water may be present as water of crystallization of the solid acid material or materials therein, or as absorbed or adsorbed water of the solid acid material (referred to as the "free water content" below). At least a portion of the water of crystallization may be removed during the steps of agitating as described herein. Moreover, water necessary for the hydrolysis of the cellulose may be provided by any moisture or water contained in the cellulose-containing material. In addition, in the hydrolysis of cellulose, a dehydration of glucose may take place to provide further water for the hydrolysis reaction.

In accordance with another aspect of the present invention, during the step (b) of agitating, the free water content of the solid acid material is in the range of about 4% to about 10% by weight of the solid acid material. The free water content of the cellulose-containing material and the solid acid material is collectively less than about 45% by weight, and preferably from about 8% to about 40% by weight, so as to not undesirably lower the kinetic energy needed for the hydrolysis reaction upon agitating. By "free water content," it is meant an amount of water in the cellulose-containing material and solid acid containing material that is contained within the cellulose-containing material and the solid acid material, but does not pertain to a water of hydration or crystallization of either material. In this way, there is sufficient water in the mixture to drive the hydrolysis reaction.

In accordance with yet another aspect of the present invention, the solid acid material is an aluminosilicate material, such as a clay material. The clay material may be any one of kaolin, bentonite, fuller's earth, or an acid-treated clay material, such as acid-treated bentonite treated with about 1 M hydrochloric acid. When the solid acid material is a clay material, the clay material may have a water content that is attributable to a water of crystallization of the material or materials therein. The water of crystallization may be removed during agitating to further provide needed water for the hydrolysis reaction.

In accordance with still another aspect of the present invention, the solid acid material is a solid superacid material. Superacids may be defined as acids stronger than 100% sulfuric acid (also known as Brönsted superacids). In addition, superacids may be described as acids that are stronger than anhydrous aluminum trichloride (also known as Lewis superacids). Solid superacids are composed of solid media that are treated with either Brönsted or Lewis acids. In one embodiment, the solid acid is a solid superacid comprising alumina treated with 2 M sulfuric acid, filtered and calcined at about 800° C. for about 5 hours.

In accordance with another aspect of the present invention, the ratio of the cellulosic-containing material to the solid acid material is from about 0.5:1 to about 10:1. When the solid acid material is a clay material, in one embodiment, the ratio of the cellulosic material to the solid acid material may be provided in the range of from about 1:1 to about 3:1 because the clay material contains a free water content, as well as water of crystallization.

In accordance with another aspect of the present invention, the cellulose-containing material is a lignocellulosic material. As a result of the steps (a) and (b) of contacting and agitating in any embodiment described herein, the hemicellulose is hydrolyzed into a quantity of soluble sugars and the lignin is decomposed into useful aromatic hydrocarbons, such as vanillin. The soluble sugars from the hydrolysis of hemicellulose and the produced aromatic hydrocarbons may be recovered in a first aqueous solution after the step of agitating from the cellulose-containing material and the solid acid material. This first aqueous solution may also comprise soluble sugars from the hydrolysis of cellulose. In addition, the solid acid material and the lignocellulosic material may be rinsed with an aqueous solution to produce a second aqueous solution comprising soluble sugars, as well as the aromatic hydrocarbons. Thereafter, the solid acid material may be reused to hydrolyze further lignocellulosic material when combined with additional cellulose-containing material.

Polysaccharides are polymeric carbohydrate structures formed of repeating units (either mono- or di-saccharides) joined together by glycosidic bonds. Cellulose is a polysaccharide that has a general formula of $(C_6H_{10}O_5)_n$ where n is typically 40-3000. When traditional acid hydrolysis is used for production of fermentable sugars from cellulose containing materials, the resulting polysaccharide oligomers range from n=1 to n=7. The inventors have found that mechnocatalytic acid hydrolysis according to the methods taught herein consistently produces a polysaccharide oligomer material wherein the material contains at least a majority of polysaccharide oligomers having an n no greater than n=2. In a more specific embodiment, the polysaccharide oligomer content of the product of hydrolyzing the cellulose-containing material comprises 70 percent or more oligomers having a n no greater than 2. In an even more specific embodiment the polysaccharide oligomer content comprises at least 80 percent, at least 85 percent, at least 90 percent, at least 95 percent or 100 percent of oligomers having an n no greater than n=2. Thus, based on this, and in view of the teachings herein, those skilled in the art will be enabled to identify a hydrolyzed product produced according to embodiments of the present invention. Furthermore, the ability to breakdown cellulose into polysaccharide oligomers of such a small size provides a material comprising a higher yield of fermentable sugars. This, of course, equates to higher efficiencies and lower cost for producing ethanol and other products from cellulose.

According to other certain method embodiments, the hydrolyzed product possesses a specific sugar profile. Thus, according to one embodiment, the invention pertains to a hydrolyzed product (typically in the form of a liquid suspension) of hydrolysis of a cellulose-containing material comprising 3 or more of the following: cellobiose, glucose, fructose levoglucosan levoglucosenone, furfural, and 5-hydroxymethylfurural. In another embodiment, the hydrolyzed product comprises levoglucosenone and/or furfural. In an even more specific embodiment, the hydrolyzed product comprises levoglucosenone and furfural. The inventors have determined that such components are not produced by the conventional techniques of acid hydrolysis or enzymatic hydrolysis of cellulose-containing materials. Accordingly, based on this, and in view of the teachings herein, those skilled in the art will be enabled to identify a hydrolyzed product produced according to embodiments of the present invention.

Upon hydrolysis according to certain embodiments of the invention, the resultant product is then either directly subjected to fermentation (according to convention techniques) or is subjected to an intermediate enzymatic hydrolysis step.

These and other advantages will be apparent from the disclosure of the invention(s) contained herein.

As used herein, "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The above-described embodiments and configurations are neither complete nor exhaustive. As will be appreciated, other embodiments of the invention are possible utilizing, alone or in combination, one or more of the features set forth above or described in detail below.

BRIEF DESCRIPTION OF THE DRAWINGS

The invention is explained in the following description in view of the drawings that show.

DETAILED DESCRIPTION OF THE INVENTION

Figure 1:
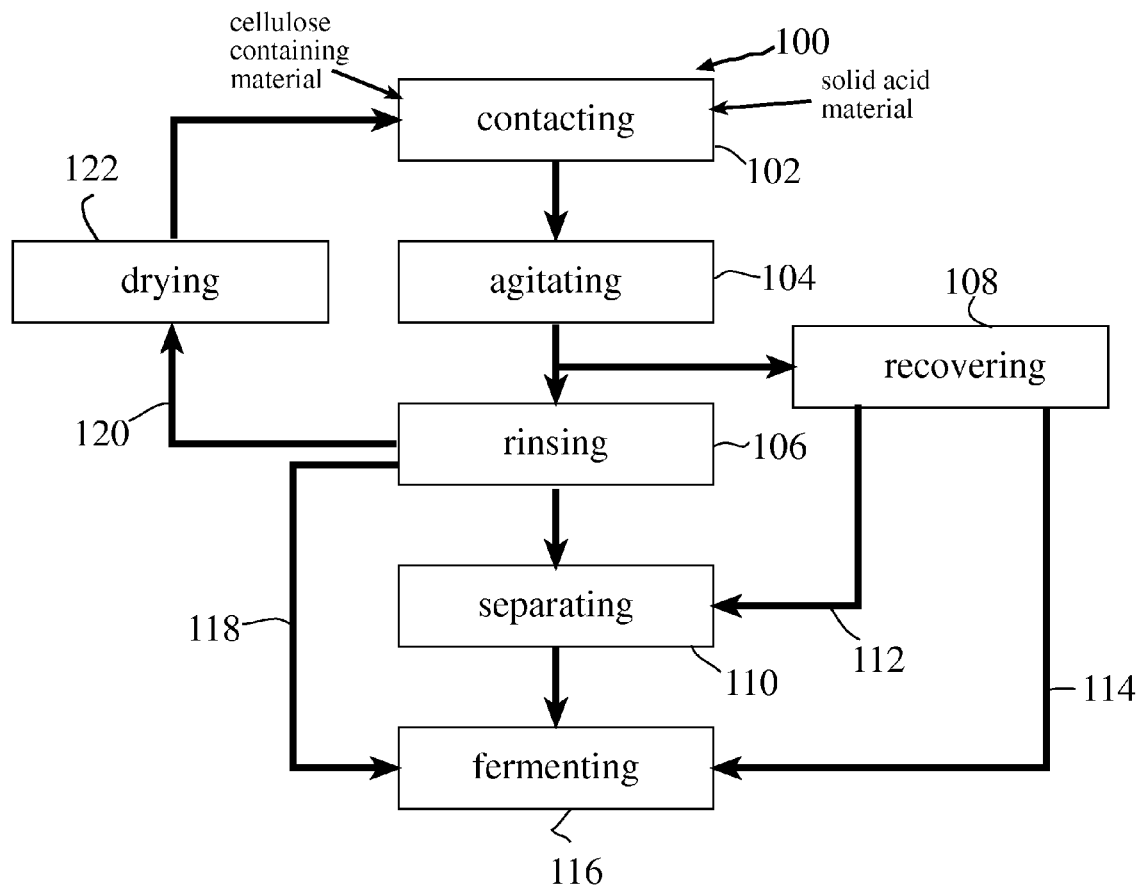
FIG. 1 is a flow schematic of one embodiment of the present invention.

Now referring to the figures, FIG. 1 shows a schematic representation of a process 100 for the production of soluble and fermentable sugars from a cellulose-containing material in accordance with one aspect of the present invention. In step 102, a quantity of a cellulose-containing material is contacted with a quantity of a solid acid material. To accomplish this, the materials may be introduced into any suitable vessel, and preferably the vessel in which the step of agitating will take place, by any suitable method, and simultaneously or sequentially one after the other. While not necessary, it is contemplated that the cellulose-containing material may be pretreated as desired, such as by breaking or grinding the material down to a desired size, before bringing the cellulose-containing material and solid acid material into contact with one another.

The cellulose-containing material may be any material or mixture of materials having a cellulose content. Thus, in one embodiment, the cellulose-containing material may be a purified source of cellulose. In another embodiment, the cellulose-material is a natural cellulosic feedstock, typically referred to as a "biomass." Exemplary biomass materials include wood, paper, switchgrass, wheat straw, agricultural plants, trees, agricultural residues, herbaceous crops, starches, corn stover, saw dust, and high cellulose municipal and industrial solid wastes.

In one embodiment, the biomass material is a lignocellulosic material having a cellulose, hemicellulose, and lignin content. Typically, in such lignocellulosic material, the cellulose, hemicellulose, and lignin are bound together in a complex gel structure along with small quantities of extractives, pectins, protein, and ash. As discussed above, generally, lignocellulosic material is poorly accessible to microorganisms, yeast, and enzymes, and the like that are sometimes used to hydrolyze cellulose. A substantial benefit of the present invention is that when the cellulose-containing material is a lignocellulosic material, the lignin and hemicellulose can also be broken down into useful products by the solid acid material of the present invention, thereby eliminating waste from the process and eliminating the need to purify the cellulose material before hydrolyzing the material. Any quantity of cellulose-containing material may be provided in the present invention in the ratios set forth herein.

The solid acid material may be any solid material having a surface acidity. By "solid," it is meant a solid material, a semi-solid material, or any other material having a water content of less than about 40% by weight. Surface acidity refers to the acidity of the solid surface of the material. Surface acidity determination methods are founded on the adsorption of a base from the base's solution. The amount of base that will cover the solid surface of the solid acid material with a monolayer is defined as the surface acidity and corresponds to the $pK_a$ of the based used. The base used may be n-butylamine, cyclohexamine, or any other suitable base. The degree of surface acidity is typically expressed by the Hammet and Deyrups $H_0$ function.

$$H_0 = pK_{BH+} - \log(C_{BH+}/C_B) \quad (I)$$

Thus, in this equation, when an indicator, B, is adsorbed on an acid site of the solid surface of the material, a part of the indicator is protonated on the acid site. The strength of the acid sites may be represented by Formula (I) by the value of $pK_{BH+}$ of $BH^+$. $BH^+$ is the conjugate acid of indicator B when the concentration of $BH^+$($C_{BH+}$) is equal to the concentration of B ($C_B$). Therefore, the acid strength indicated by $H_0$ shows the ability of the conjugate to change into the conjugate acid by the acid sites that protonates half of the base indicator B. Under a Lewis definition, the $H_0$ value shows the ability that the electron pair can be received from half of the absorbed base indicator B. See Masuda et al., Powder Technology Handbook, $3^{rd}$ Ed. (2006). A $H_0$ of −8.2 corresponds to an acidity of 90% sulfuric acid and a $H_0$ of −3.0 corresponds to an acidity of about 48% sulfuric acid.

Any suitable method of determining the $H_0$ of a material may be used, such as the method using the adsorption of n-butylamine from its solution in cyclohexane as set forth in *Investigation of the Surface Acidity of a Bentonite modified by Acid Activation and Thermal Treatment*, Turk. J. Chem., 2003; 27:675-681, the disclosure of which is hereby incorporated by reference in its entirety. Alternatively, indicators, generally referred to as Hammett indicators, may be used to determine the $H_0$ of a material. Hammett indicators rely on color changes that represent a particular surface acidity of the subject material.

In the present invention, a number of solid acid materials may be used. Generally, the solid acid material in the present invention may be any solid material having a surface acidity. Preferably, the solid acid material has an $H_0$ of less than about −3.0, and preferably less than about −5.6.

In one embodiment, the solid acid material is a clay material. As used herein, "a clay material" is defined as a material composed primarily of fine-grained minerals, which is generally plastic at appropriate water contents and will harden with dried or fired. Exemplary minerals that comprise the major proportion of clay materials for use in the present invention include kaolinite, halloysite, attapulgite, montmoirllonite, illite, nacrite, dickite, and anauxite. Non-limiting examples of clays for use in the present invention include fuller's earth, kaolin, and bentonite. Kaolin is a clay material that mainly consists of the mineral kaolinite. Bentonite is a clay containing appreciable amounts of montmorillonite, and typically having some magnesium and associated therewith. Optionally, the clay material may be acid-treated to provide further surface acidity to the clay material.

In another embodiment, the solid acid material is any aluminosilicate or hydrated aluminosilicate mineral. For example, the solid acid may be vermiculite, muscovite mica, kaolinite, halloysite, attapulgite, montmorillonite, illite, nacrite, dickite, and anauxite, or zeolites such as analcime, chabazite, heulandite, natrolite, phillipsite, and stilbite, or any mineral having the general formula $Al_2O_3.xSiO_2.nH_2O$.

In another embodiment, the solid acid material is a superacid material. Superacid materials are useful in the present invention because of the high number of acidic sites on the surface of the superacid material. Brönsted superacids may be described as acids which are stronger than 100% sulfuric acid. Lewis superacids may be described as acids that are stronger than anhydrous aluminum trichloride. Solid superacids are composed of solid media, i.e. alumina, treated with either Brönsted or Lewis acids. The solids used may include natural clays and minerals, metal oxides and sulfides, metal salts, and mixed metal oxides. Exemplary Brönsted superacids include titanium dioxide:sulfuric acid ($TiO_2:H_2SO_4$) and zirconium dioxide:sulfuric acid ($ZrO_2:H_2SO_4$) mixtures. Exemplary Lewis superacids involve the incorporation of antimony pentafluoride into metal oxides, such as silicon dioxide ($SbF_5:SiO_2$), aluminum oxide ($SbF_5:Al_2O_3$), or titanium dioxide ($SbF_5:TiO_2$). In one embodiment, the superacid is a metal oxide treated with treated with either Brönsted or Lewis acids. In a particular embodiment, the superacid is alumina treated with sulfuric acid as set forth below.

Alternatively, the solid acid material may be a silicate material, such as talc or any other suitable solid material having a surface acidity, such as alumina, and combinations of any of the materials described herein.

Figure 2:
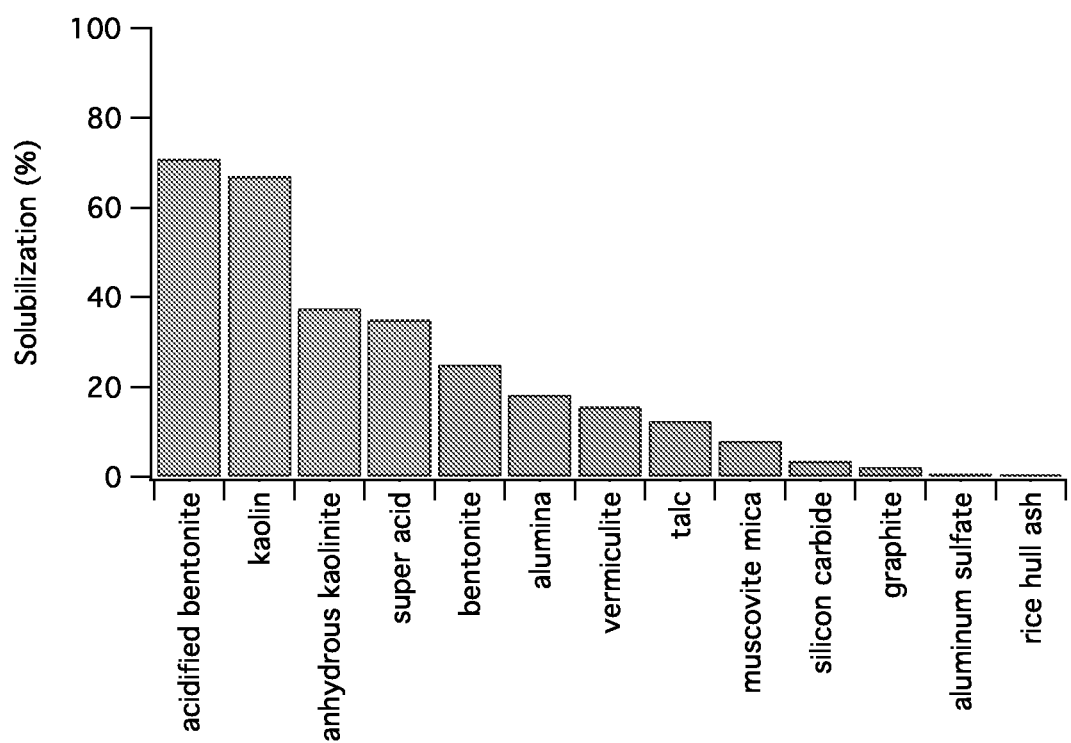
FIG. 2 shows the solubilization efficiency of various solids after three hours of milling in accordance with the present invention.

As shown in FIG. 2, the solubilization efficiency for a number of materials was compared for the solubilization of cellulose after three hours of milling in a SPEX 8000D mixer mill available from SPEX CertiPrep of Metuchen, N.J. The materials that provided the best results were those material having a surface acidity value ($H_0$) of less than about −3.0. Acidified bentonite, kaolin, anhydrous kaolinite, a super acid in the form of aluminum oxide treated with sulfuric acid, all have $H_0$ values of less than about −3.0. Acidified bentonite and kaolin provided the best solubilization efficiencies, followed by anhydrous kaolinite, a super acid in the form of aluminum oxide treated with sulfuric acid, bentonite, alumina, vermiculite, muscovite mica, talc, silicon carbide, graphite, aluminum sulfate, and rice hull ash. Silicon carbide, graphite, aluminum sulfate, and rice hull ash are known not to have any appreciable surface acidity.

Since kaolin provided a high degree of solublization, specifically, a solublization efficiency for cellulose of at least about 70%, in one embodiment, the solid acid material is kaolin. Kaolin is composed primarily of the mineral kaolinite. Kaolinite ($Al_2Si_2O_5(OH)_4$) is a layered silicate made of alternating sheets of octahedrally coordinated aluminum and tetrahedrally coordinated silicon that are bonded by hydroxyl groups. Alternatively, the solid acid may be in the form of anhydrous kaolin, which may be prepared by heating kaolin at about 800° C. for at least about 6 hours and preferably at about 800° C. for about 8 hours.

In another embodiment, the solid acid is bentonite, and preferably acidified bentonite. Bentonite is an absorbent aluminum phyllosilicate generally impure clay consisting mostly of montmorillonite, $(Na,Ca)_{0.33}(Al,Mg)_2Si_4O_{10}(OH)_2 \cdot (H_2O)_n$. Two types exist: swelling bentonite which is also called sodium bentonite and non-swelling bentonite or calcium bentonite. Preferably, the bentonite is non-swelling bentonite. The acidified bentonite may be prepared by treating bentonite with one or more acids, such as by treating bentonite with 1 M hydrochloric acid solution.

In still another particular embodiment, the solid acid is a solid superacid comprising alumina treated with 2 M sulfuric acid, filtered and calcined at about 800° C. for about 5 hours.

Kaolin and acidified bentonite are desirable materials for use in the present invention because they provide a high surface acidity along with an inherent an amount of water, both due to a water of crystallization and a free water content, which are both useful to hydrolyze the glycosidic bonds of the cellulose material. Therefore, using acidified bentonite, bentonite, and kaolin as the solid acid material can provide a substantial benefit as the use of the materials may eliminate the need for added water to the solubilization process, thereby significantly decreasing time and expense in the solubilization of cellulose.

Accordingly, in one embodiment, the free water content of the solid acid material is from about 4% to about 10% by weight. Kaolin and bentonite generally have a free water content of greater than about 4% by weight, as well as a water of crystallization content. Water of crystallization refers to water that occurs as a constituent of crystalline substances in a definite stoichiometric ratio. This water can be removed from the substances by the application of heat at about 700° C. and its loss usually results in a change in the crystalline structure. In the present invention, it is believed that the agitating step as described herein provides the localized heat necessary to remove the water, including water of crystallization, from the solid acid material (when water of crystallization is present) to provide further water for the hydrolysis of the cellulose-containing material.

The water content of most compounds, including the water of crystallization of the subject material, can be determined by thermogravimetric analysis (TGA), where the sample is heated, and the accurate weight of a sample is plotted against the temperature. Alternatively, any other suitable method for determining water content may be used, including mass loss on heating, Karl Fischer filtration, and freeze drying, or any other suitable method.

Figure 4:
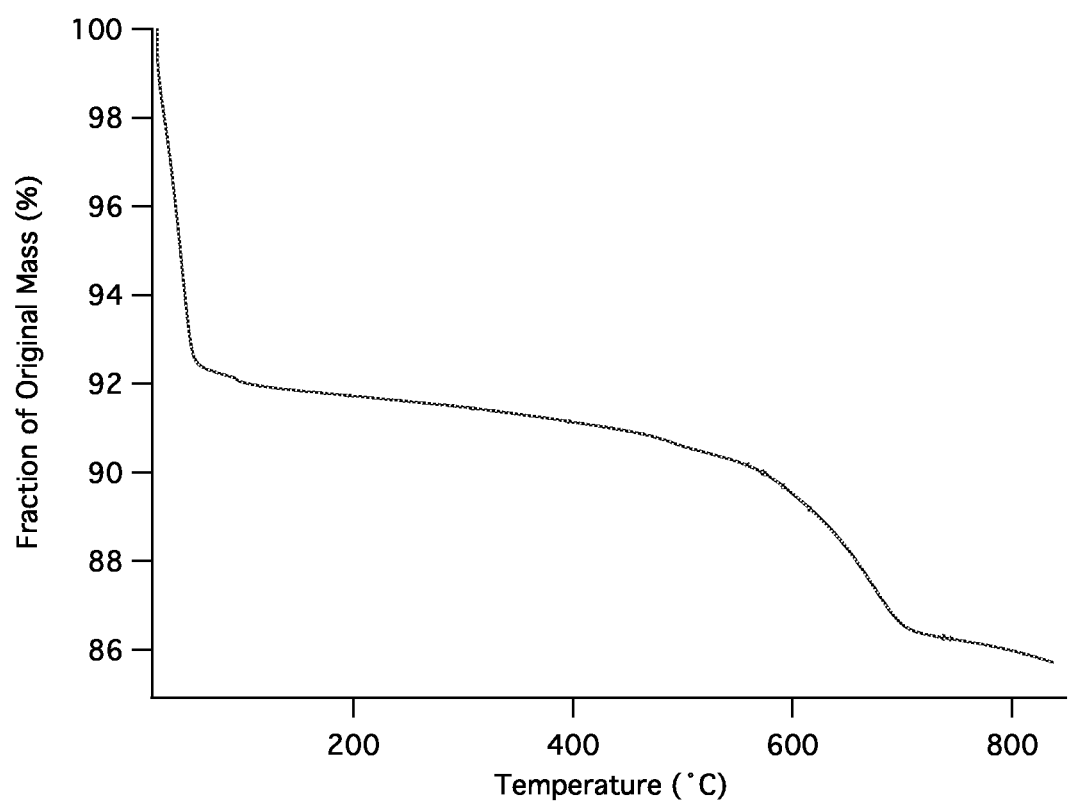
FIG. 4 shows the water content of bentonite through the mass loss of bentonite by heating the bentonite material.

As shown in FIG. 4, heating 5 milligrams of bentonite to a temperature of 850° C. at a rate of 10° C./minute showed a water loss of from about 7.0 to about 7.5% by mass at 100° C. for adsorbed water and an additional mass loss of another about 5% to about 6% by mass due to the water of crystallization. It is believed that kaolin has a similar free water content relative to bentonite. As discussed above, the water of crystallization and the free water content of the clay materials are useful for the hydrolysis of the cellulosic glycosidic bond in the processes of the present invention.

In another embodiment, the solid acid material is an acid-treated material, such as sulfuric acid-treated alumina to form a superacid. To prepare this superacid, alumina was stirred in 2 M sulfuric acid, filtered and calcined at about 800° C. for about 5 hours. Treating the alumina with sulfuric acid adds sulfate ions to the solid alumina surface, thereby allowing the solid acid material to further accept electrons. As a result, these superacids have a very high surface acidity. However, while superacids may have a higher surface acidity than bentonite or kaolinite, the superacids may not have as much water present. As a result, while not wishing to be bound by theory, it appears the additional water content found in kaolin and bentonite contributes to the higher solubilization efficiency for cellulose found with bentonite or kaolonite over acid-treated alumina. This statement is further supported in showing that the solubilization efficiency is lower for anhydrous kaolinite vs. kaolin, which has a higher water content.

The ratio of the cellulose-containing material to the solid acid material is such that the solubilization of cellulose is optimized. Generally, the solubilization efficiency is optimized by determining a ratio of the cellulose-containing material to the solid acid material, wherein a surface interaction of the solid acid and cellulose-containing material is maximized and the combined water content of the cellulose material and solid acid material is optimized. If there is too much moisture in the combined cellulose-containing material and the solid acid material, or the individual materials during agitating of the materials, the amount of kinetic energy available to drive the hydrolysis of cellulose is lowered and the process results in a lowered yield of soluble and fermentable sugars. On the other hand, incomplete solubilization of the cellulose-containing material results if the water content is too low.

Figure 6:
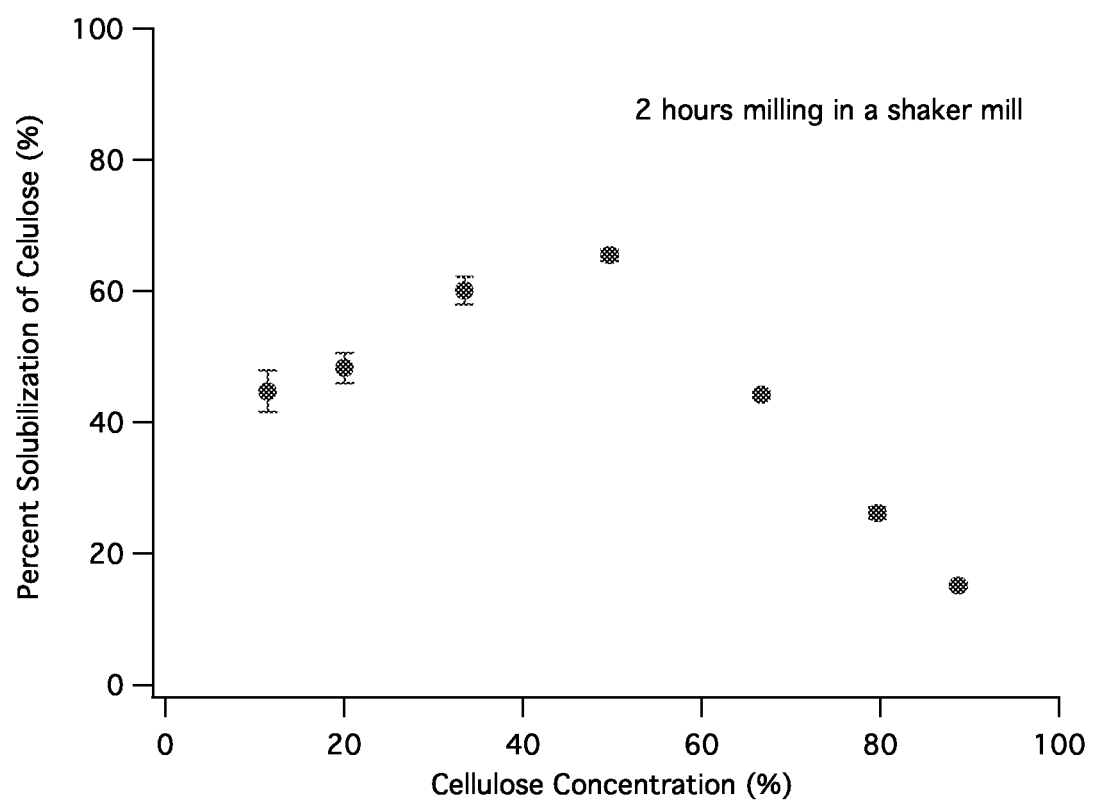
FIG. 6 shows the optimal ratio of cellulose to kaolinite for solubilizing cellulose.
Figure 7:
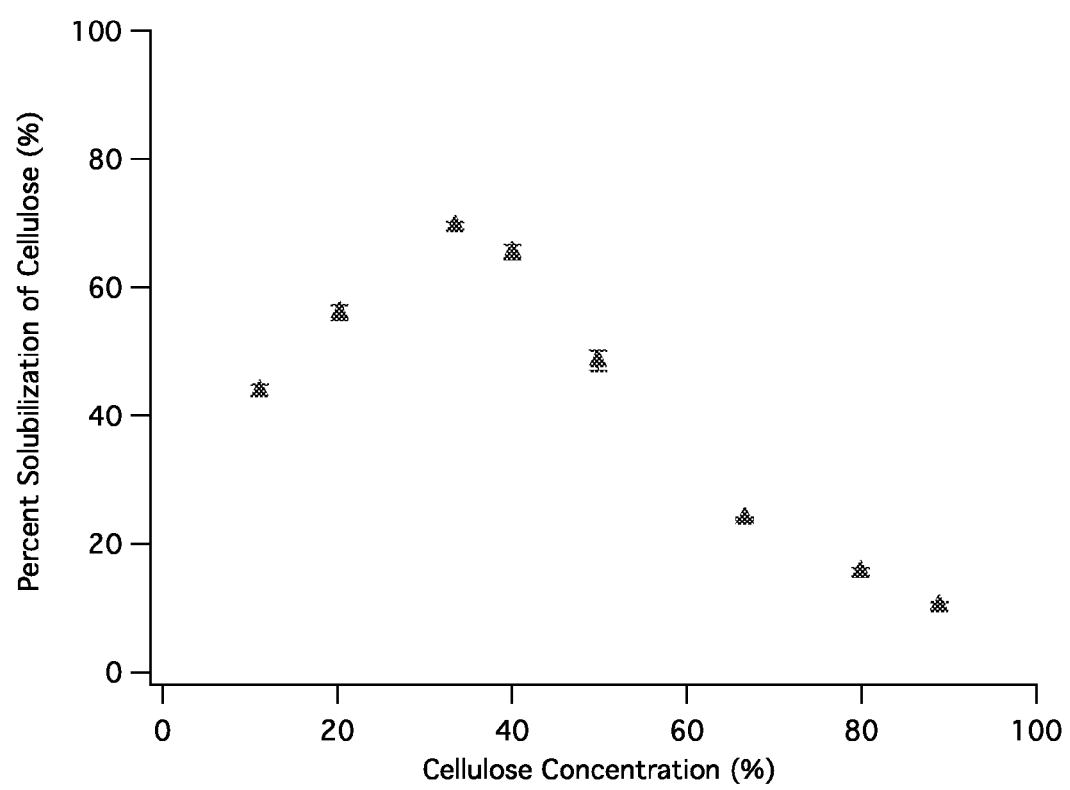
FIG. 7 shows the optimal ratio of cellulose to bentonite for solubilizing cellulose.

In one embodiment, the cellulose-containing material is provided in a ratio of from about 0.5:1 to about 10:1 cellulose-containing material to solid acid material. In a particular embodiment, when the solid acid material is kaolin, FIG. 6 shows that the optimal yield of soluble and fermentable sugars is obtained with about an 1:1 mass ratio of cellulose to kaolin after about 2 hours of milling in a SPEX 8000D shaker mill available from SPEX CertiPrep of Metuchen, N.J. The material was milled in 0.5 hour increments in 50 mL milling vials constructed of 440C stainless steel with 3 440C steel balls ½" diameter as the milling media. Similarly, FIG. 7 shows that the optimal yield of soluble and fermentable sugars is obtained with a 1:2 mass ratio of cellulose to bentonite after two hours of milling in a SPEX 8000D shaker mill. The material was milled in 0.5 hour increments in 50 mL milling vials constructed of 440C stainless steel with 3 440C steel balls ½" diameter as the milling media.

Figure 5:
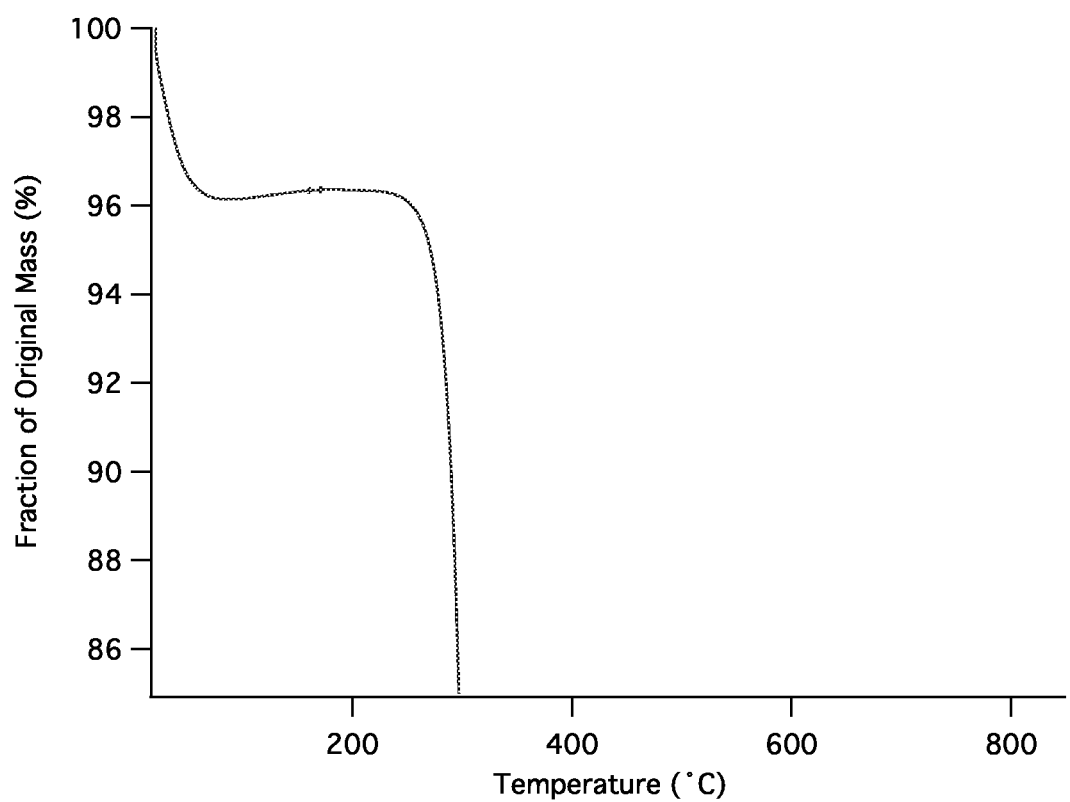
FIG. 5 shows the mass loss of cellulose upon heating indicating an adsorbed moisture content of about 4% by weight.

In one embodiment, the cellulose-containing material has a free water content of from about 4% to about 40% of the cellulose-containing material. As shown in FIG. 5, by heating 3.5 milligrams of 100% pure cellulose (Avicell microcrystalline cellulose, obtained from Fisher Scientific) to a temperature of about 850° C. at a rate of about 10° C./min. The mass loss at about 100° C. indicated an adsorbed moisture content of about 4%.

From calculations, it is known that to convert 100% cellulose to 100% fructose or glucose, the minimum water required is 4.76% by weight. Thus, when the cellulose-containing material and the solid acid are contacted in step 102, in one embodiment, the free water content of the collective mixture is less than about 45% by weight of the materials, and more preferably from about 8% to about 40% by weight of the materials. In this way, a sufficient water content is provided to drive the hydrolysis of cellulose at ambient temperature and without the requirement of added water. This may result in huge savings to one performing the processes described herein on a large, manufacturing scale. Optionally, however, water may added as needed at any of the steps of the processes described herein to provide the necessary water content to drive the hydrolysis reaction.

In step 104, the cellulose-containing material and the solid acid material are agitated for a time sufficient to provide a product comprising a quantity of soluble sugars. The agitation may take place in any suitable vessel or reactor. In one embodiment, the agitating takes place in a ball, roller, jar, hammer, or shaker mill. The mills generally grind samples by placing them in a housing along with one or more grinding elements and imparting motion to the housing. The housing is typically usually cylindrical and the grinding elements are typically steel balls, but may be rods, cylinders, or other shapes. Generally, the containers and grinding elements are made from the same material.

As the container is rolled, swung, vibrated, or shaken, the inertia of the grinding elements causes the grinding elements to move independently into each other and against the container wall, grinding the sample. In one embodiment, the mill is a shaker mill using steel balls and shaking to agitate the cellulose-containing material and the solid acid material. The mills for use in the present invention may range from those having a sample capacity of a gram or less to large industrial mills with a throughput of tons per minute. Such mills are available from SPEX CertiPrep of Metuchen, N.J., for example Paul O. Abbe, Bensenville, Ill., or Union Process Inc., Akron, Ohio. For some mills, such as a steel ball mill from Paul O. Abbe, the optimal fill volume is about 25% of the total volume of the mill. The number of steel balls required for the process is dependant upon the amount of kinetic energy available. High energy milling like that in a shaker mill require less balls than lower energy milling methods such as rolling mills. For shaking mills, a ball to sample mass ratio of about 12:1 is sufficient. For rolling mills, a ball to sample mass ratio of about 50:1 works well for a rolling rate of about 100 rpm. Lower mass ratios can be obtained by increasing the amount of kinetic energy available to the system. In a roller mill, this can be achieved through optimization of mill geometry and/or increasing the mill's rotational velocity.

A significant advantage of the present invention is that the processes described herein can be performed at ambient temperature without the need for added heat, cooling, or modifying pressure. Instead, the processes, including the agitation step, can be performed under ambient conditions. Without wishing to be bound by theory, it is believed the agitating of the cellulose-containing material with the solid acid material, such as in with the aforementioned mills, provides the process with the energy required for the hydrolysis of the cellulose, and cellulose, hemicellulose and lignin if the cellulose-containing material is a lignocellulosic material. Moreover, it is believed the agitating also allows more of the cellulose-containing material to contact the acidic sites on the surface of the solid acid material. Even further, it is believed that the heat created by the agitating frees up the inherent water content of the material contained as water of crystallization of the material to provide water fro the hydrolysis reaction. In an alternate embodiment, the agitating may occur at a controlled temperature of between about −5 to about 105 degrees C. It is contemplated that agitation may occur at any temperature degree value within this range (rounded to the nearest 0.5 centigrade unit), or within any sub-ranges within this range (rounded to the nearest 0.5 centigrade unit).

After the step of agitating 104, a first aqueous solution is optionally removed from the vessel where the agitating is performed in recovering step 108 as shown. Typically, this aqueous solution will comprise an aqueous solution of soluble sugars, typically in the form of monosaccharides, disaccharides, and polysaccharides. When the cellulose-containing material is a lignocellulosic material, this aqueous solution may also comprise further soluble sugars, as well as useful aromatic hydrocarbons, such as vanillin. Vanillin is a known flavoring additive in the food industry. It is contemplated that the first aqueous solution may also comprise other byproducts of the decompositions reaction which occur, such as hydroxymethylfurfural or HMF. Hydroxymethylfurfural is an aldehydic compound that is found in a number of foods, such as milk, fruit juices, spirits, and honey. Thus, in one embodiment, the processes as described herein can also be used for the production of furfurals, namely HMF, and also vanillin. For example, glucose produced by the hydrolysis of cellulose can be used as a starting material to produce furfurals by dehydration of the glucose compounds. The production of HMF may be enhanced by the use of solid acids that incorporate transition metals such as, but not limited to chromium and molybdenum.

Preferably, after the step of agitating 104, the cellulose-containing material and solid acid material are rinsed with an aqueous solution as set forth below in step 106. Alternatively, from recovering step 108, at least a portion of the first aqueous solution is optionally directed to a separating step 110 as indicated by arrow 112, where any separation of the components of the first aqueous solution can be performed by any suitable technique known in the art. For example, if vanillin is desired to be separated out from the solution, the vanillin can be removed by any suitable method, such as by chromatographic methods well known in the art. Further alternatively, at least a portion of the first aqueous solution may be directed to fermenting step 116 as described below and indicated by arrow 114.

When using a mill as described herein, the hydrolysis processes described herein are generally carried out as a batch process. In addition, the vessel where the agitating and hydrolysis reaction takes place may be performed in a continuous attritter, which is commercially available from Union Process, Akron, Ohio. This device more generally allows the process to be carried out as a continuous process.

A significant advantage of the present invention is that the vessel where the agitation takes place will generally provide the necessary heat and kinetic energy to drive the hydrolysis reaction. As such, it is generally not necessary to add any heat to the processes as described herein and the agitating may take place at ambient temperature. As described above, however, in an alternate embodiment, the agitating may occur at a controlled temperature of between about −5 to about 105 degrees C. The agitating step 104 also ensures that the acidic sites on the surface of the solid acid material interact with the cellulose-containing material in order to promote decomposition of the cellulose, and hemicellulose and lignin, if present. When the material is a clay material or other material having a water of crystallization, the agitating may free up water for use in the hydrolysis reaction.

Figure 3:
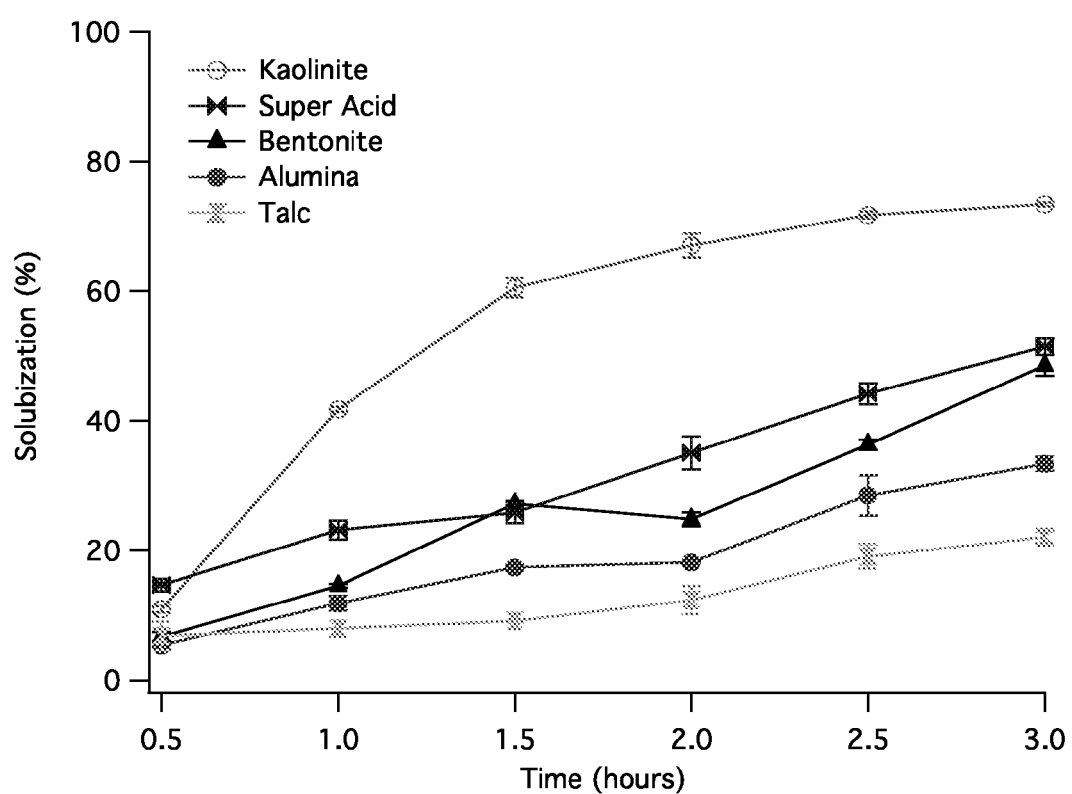
FIG. 3 shows the effect of milling time on the solubilization of cellulose.

The milling time can have an effect on the extent of solubilization of the cellulose material. For example, as shown in FIG. 3, kaolin approaches a maximum percent of solubilization after about two hours of shaker milling in a sealed hardened steel vial with a ball to sample mass ratio of 12:1. Other materials may not have reached their maximum after three hours of milling, the bulk of which may be fermentable into ethanol. As is also shown in FIG. 3, sulfuric acid-treated alumina, bentonite, alumina, and talc had not yet reached a maximum after three hours of shaker milling in a sealed hardened steel vial with a ball to sample mass ratio of 12:1.

Figure 8:
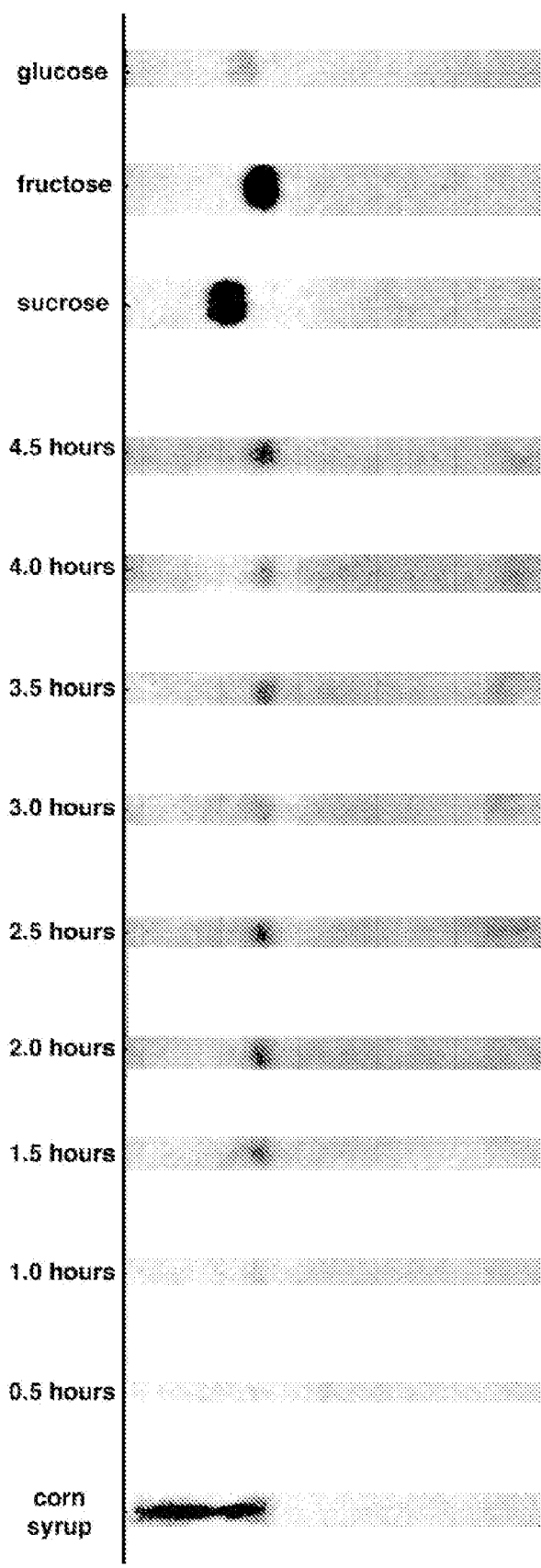
FIG. 8 shows the progression of the solubilization of cellulose and the soluble sugars produced over time on a thin-layer chromatography plate during a process in accordance with the present invention.

As shown in FIG. 8, 1 gram of cellulose and 1 gram of kaolin were milled in hardened steel vials with 0.5" steel balls and a ball to sample mass ratio of 12:1. The agitation was supplied by a SPEX 8000D mixer mill available from SPEX CertiPrep of Metuchen, N.J. The production of soluble sugars was monitored over a time period of 4.5 hours by thin-layer chromatography using an EMD Chemicals cellulose TLC plate, 20 cm×10 cm. A developing solution was used that consisted of a mixture of butanol, water, and acetic acid. The oligosaccharides were stained by spraying with a urea-phosphoric acid solution and heating to about 80° C. for about 10 minutes. This stain colors ketoses blue and aldoses a pale red. Individual samples were prepared by milling samples with a total mass of 2 grams for the prescribed amount of time in ½ hour increments.

As can be seen by FIG. 8, a notable amount of fructose is increasingly formed during the reaction, in addition to glucose. In addition, the agitating step 104 may produce a further quantity of soluble sugars, including sugars in the form of monosaccharides, disaccharides and polysaccharides. For example, the solubilized sugars may be polysaccharides up to eight glucose units. In addition, other byproducts may be formed in the agitating step 104, such as furfurals from the dehydration of glucose and small quantities of ethanol. If ethanol is formed, the ethanol may be removed from the mill by any suitable method, such as by vacuum distillation, as the ethanol is formed. If the cellulose-containing material is a hemicellulose material, the agitating step 104 may also produce further soluble sugars or long-chain sugars, as well as aromatic hydrocarbons and furfurals, such as HMF. The majority of soluble sugars produced by the processes described herein are suitable for use in fermenting processes to produce ethanol.

It is contemplated that at least about 80% of the cellulose in the cellulose-containing material may be solubilized in embodiments of the present invention. It is appreciated that higher efficiencies may be obtained by selecting the various solid acids, milling time, and modifying the ratio of the cellulose-containing material to the solid acid material. If relatively pure cellulose is used, it is contemplated that less cellulose-containing material may be required than if the cellulose-containing material were a biomass material, such as lignocellulose.

Referring again to FIG. 1, after step 104 of agitating, the cellulose-containing material and solid acid material may be washed with an aqueous solution in step 106 to produce a second aqueous solution containing soluble sugars. The sugars may in the form of monosaccharides, disaccharides and polysaccharides. Any suitable method of determining the amount of solubilized sugars may be used, such as by chromatographic methods well known in the art. Moreover, the presence of particular solubilized sugars may be confirmed by any suitable chromatography method, such as thin-layer chromatograph, gas chromatography (GC), high-pressure liquid chromatography (HPLC), GC-MS, LC-MS, or any other suitable method known in the art. The second aqueous solution may also comprise furfurals, ethanol, aromatic hydrocarbons, such as vanillin as previously described herein.

The washing step 106 may be repeated until it is relatively certain that the bulk of the soluble sugars have been recovered in the second aqueous solution. Thereafter, the second aqueous solution may be directed to fermenting step 116 as indicated by arrow 118 or alternatively to separating step 110 for separation of any of the desired components by any suitable technique known in the art.

Since the solid acid is acting as a catalyst in the hydrolysis of the cellulose-containing material, the solid acid material may be recycled. Thus, optionally, the solid acid material may be directed to drying step 122 to dry the material a suitable moisture content, if necessary, as shown by arrow 120 and a new quantity of cellulose-containing material can be combined with the all or a portion of the recycled solid acid material to again produce a quantity of solubilized sugars. If no drying step is necessary, the rinsed solid acid material can be immediately reused in contacting step 102. In either instance, the rinsed solid acid material is optionally recycled and reused to hydrolyze further cellulose-containing material by starting the process again at step 102. Additional solid acid material may be added as needed to supplement the recycled solid acid material when redoing step 102. Accordingly, a significant advantage of the present invention is that at least a portion of the solid acid material may be reused continuously, thereby savings considered material and expense.

The recovered fermentable sugars from step 108, any portion of the first and/or second aqueous solutions, or all of the first and/or second aqueous solutions having the soluble, and mainly fermentable sugars, may then be fermented by any suitable method, to produce ethanol as indicated by step 116 of FIG. 1. For example, yeast, genetically engineered strains of *E. coli*, or other commercially available products may be used to convert the sugars to ethanol. Initially, the soluble sugars may be converted to a more desirable sugar by enzymes.

Alternatively, the soluble sugars may be directed to a process for carmelization of the soluble sugars, such as sucrose and glucose. Carmelization provides desirable color and flavor in bakery's goods, coffee, beverages, beer and peanuts. Specifically, the carmelization process can produce useful compounds, such as furans like hydroxymethylfurfural (HMF) and hydroxyacetylfuran (HAF), furanones such as hydroxydimethylfuranone (HDF), dihydroxydimethylfuranone (DDF) and maltol from disaccharides and hydroxymaltol from monosaccharides. Hydroxymethylfurfural (HMF) is found in honey, juices, milk but also in cigarettes. Thus, as well as producing a feedstock for the production of ethanol, the present invention may also provide a feedstock for the production of valuable food component, such as hydroxymethylfurfural.

EXAMPLE I 1 gram of grass (a cellulose-containing material) was combined with 1 gram of kaolinite (solid acid material). The grass was oven dried at 80° C. to a moisture content of 4% by mass. The materials were placed in a hardened 440C steel vial with 3 440C steel balls ½" in diameter. The vial was agitated at ambient temperature in a SPEX8000D mixer mill in 0.5 hour increments with 0.5 hours allowed between each milling interval for cooling. It was found that there was no difference between milling for 2 hours continuously and interval milling. The mixture was milled for a total of 2 hours. Total solubilization was measured by extracting approximately 0.1 g of the milled material with 60 mL of distilled water and filtration through a 47 mm diameter Whatman Nuclepore® track etched polycarbonate membrane filter with a pore size of 0.220 μm. The residue was dried in an 80° C. oven for 12 hours and then weighed. From this value a total solubilization of 80±3% was determined. In comparison, 2 grams of grass without any solid acid, milled under the same conditions, exhibited a solubilization of 22±3% by mass.

The present invention, in various embodiments, includes components, methods, processes, systems and/or apparatus substantially as depicted and described herein, including various embodiments, subcombinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, e.g., for improving performance, achieving ease and/or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover, though the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A solid reaction product comprising catalytic products of reaction of a solid acid and a solid cellulose-containing material, wherein a combined free water content of the solid acid and solid cellulose-containing material is from about 8% to about 40% by weight, and wherein:
   (i) at least 70 percent by weight of the solid reaction product collected immediately after the reaction between the solid acid and solid cellulose-containing material consists essentially of water soluble monosaccharides and disaccharides; and
   (ii) the solid reaction product, collected immediately after the reaction between the solid acid and solid cellulose-containing material, comprises a water content of less than or equal to 10 percent by weight.

2. The solid reaction product of claim 1, wherein at least 80 percent by weight of the solid reaction product collected immediately after the reaction between the solid acid and solid cellulose-containing material consists essentially of water soluble monosaccharides and disaccharides.

3. The solid reaction product of claim 1, wherein at least 90 percent by weight of the solid reaction product collected immediately after the reaction between the solid acid and solid cellulose-containing material consists essentially of water soluble monosaccharides and disaccharides.

4. The solid reaction product of claim 1, wherein at least 95 percent by weight of the solid reaction product collected immediately after the reaction between the solid acid and solid cellulose-containing material consists essentially of water soluble monosaccharides and disaccharides.

5. The solid reaction product of claim 1, wherein the solid reaction product collected immediately after the reaction between the solid acid and solid cellulose-containing material comprises at least three compounds selected from the group consisting of cellobiose, xylose, glucose, fructose, levoglucosan, levoglucosenone, furfural, and 5-hydroxymethylfurfural.

6. The solid reaction product of claim 1, wherein the solid reaction product collected immediately after the reaction between the solid acid and solid cellulose-containing material comprises at least one compound selected from the group consisting of cellobiose, xylose, glucose, fructose, levoglucosan, levoglucosenone, furfural, and 5-hydroxymethylfurfural.

7. The solid reaction product of claim 1, wherein the solid reaction product collected immediately after the reaction between the solid acid and solid cellulose-containing material further comprises levoglucosenone.

8. The solid reaction product of claim 1, wherein the solid reaction product collected immediately after the reaction between the solid acid and solid cellulose-containing material further comprises furfural.

9. The solid reaction product of claim 1, wherein the solid reaction product collected immediately after the reaction between the solid acid and solid cellulose-containing material further comprises furfural and levoglucosenone.

10. A composition comprising a solid reaction product obtained from a step of mechanocatalytically agitating a solid cellulose-containing material in the presence of a solid acid catalyst in the absence of added water, wherein a combined free water content of the solid acid catalyst and the solid cellulose-containing material is from about 8% to about 40% by weight, and wherein the solid reaction product collected immediately after the mechanocatalytic agitation (i) comprises levoglucosenone and furfural and (ii) has a water content less than or equal to 10 percent by weight, and at least 70 percent by weight of the solid reaction product consists essentially of water soluble monosaccharides and disaccharides.

11. The composition of claim 10, wherein the solid reaction product collected immediately after the mechanocatalytic agitation further comprises at least one compound selected from the group consisting of cellobiose, xylose, glucose, fructose, levoglucosan, and 5-hydroxymethylfurfural.

12. The composition of claim 10, wherein the solid reaction product is made by a mechanocatalytic process comprising the steps of: (a) contacting the solid cellulose-containing material with the solid acid catalyst and a milling media; and (b) agitating the solid cellulose-containing material, the solid acid catalyst, and the milling media at a temperature of between about −5° to about 105° Celsius for a time sufficient to produce the solid reaction product, wherein at least 70 percent of the solid reaction product collected immediately after the reaction between the solid acid and solid cellulose-containing material consists essentially of soluble monosaccharides and disaccharides, and a water content of less than or equal to 10 percent by weight, wherein a combined free water content of the solid cellulose-containing material and the solid acid catalyst is from about 8% to about 40% by weight.

13. A solid reaction product comprising catalytic products of reaction of a solid acid and a solid cellulose-containing material, wherein a combined free water content of the solid acid and the solid cellulose-containing material is from about 8% to about 40% by weight, and wherein:
  (i) at least 70 percent by weight of the solid reaction product collected immediately after the reaction between the solid acid and solid cellulose-containing material consists essentially of glucose and xylose; and
  (ii) the solid reaction product collected immediately after the reaction between the solid acid and solid cellulose-containing material comprises a water content of less than or equal to 10 percent by weight.

* * * * *